United States Patent [19]
Young et al.

[11] Patent Number: 5,945,310
[45] Date of Patent: Aug. 31, 1999

[54] DNA ENCODING MEMBERS OF THE IL-1 FAMILY, IL-1 DELTA

[75] Inventors: Peter Ronald Young, Lawrenceville, N.J.; Ian E. James, Ardmore; Janice R. Connor, Fort Washington, both of Pa.

[73] Assignee: SmithKline Beecham Corporation, Philadelphia, Pa.

[21] Appl. No.: 08/939,300

[22] Filed: Sep. 29, 1997

Related U.S. Application Data

[60] Provisional application No. 60/046,957, May 19, 1997.

[51] Int. Cl.$^6$ .............................. C12N 15/24; C12N 15/00

[52] U.S. Cl. .................. 435/69.52; 435/69.5; 435/252.3; 435/320.1; 536/23.5

[58] Field of Search ........................... 536/235; 435/69.5, 435/69.52, 252.3, 320.1

[56] References Cited

PUBLICATIONS

Okamura et al, Nature 378, Nov. 1995, pp. 88–91.
Bazan et al *Nature* 379, Feb. 1996, p. 591.
EST #78362.

*Primary Examiner*—Garnette D. Draper
*Attorney, Agent, or Firm*—William T. Han; Ratner & Prestia; William T. King

[57] ABSTRACT

IL-1 delta polypeptides and polynucleotides and methods for producing such polypeptides by recombinant techniques are disclosed. Also disclosed are methods for utilizing IL-1 delta peptides are polynucleotides in the design of protocols for the treatment of chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease, among others, and diagnostic assays for such conditions.

11 Claims, No Drawings

DNA ENCODING MEMBERS OF THE IL-1 FAMILY, IL-1 DELTA

This application claims the benefit of U.S. Provisional Application No. 60/046,957, filed May 19, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Interleukin-1 family, hereinafter referred to as IL-1 delta. The invention also relates to inhibiting or activating the action of such polynucleotides and polypeptides.

BACKGROUND OF THE INVENTION

Interleukin-1 refers to two proteins (IL1α and IL1β) which play a key role early in the inflammatory response [for a review see C. A. Dinarello, Blood, 87:2095–2147 (1996) and references therein]. Both proteins are made as 31 kDal intracellular precursor proteins which are cleaved upon secretion to yield mature carboxy-terminal 17 kDal fragments which are biologically active. In the case of IL-1β, this cleavage involves an intracellular cysteine protease, known as ICE, which is required to release the active fragment from the inactive precursor. The precursor of IL-1α is active.

These two proteins act by binding to cell surface receptors found on almost all cell types and triggering a range of responses either alone or in concert with other secreted factors. These range from effects on proliferation (e.g., of fibroblasts, T cells), apoptosis (e.g., A375 melanoma cells), cytokine induction (e.g., of TNF, IL1, IL8), receptor activation (e.g., E-selectin), eicosanoid production (e.g., PGE2) and the secretion of degradative enzymes (e.g., collagenase). To achieve this, IL-1 activates transcription factors such as NF-κB and AP-1. Several of the activities of IL-1 action on target cells are believed to be mediate through activation of kinase cascades that have also been associated with cellular stresses, such as the stress activated MAP kinases JNK/SAPK and p38.

A third member of the IL-1 family was subsequently discovered which acts as a natural antagonist of IL-1α and IL-1β by binding to the IL-1 receptor but not transducing an intracellular signal or a biological response. The protein was called IL-1ra (for IL-1 receptor antagonist) or IRAP (for IL-1 receptor antagonist protein). At least three alternatively spliced forms of IL-1ra exist: one encodes a secreted protein, and the other two encode intracellular proteins. The relative role of the three forms and reason for their different localization is not known. All three proteins, IL-1α, IL-1β and IL-1ra, share approximately 25–30% amino acid identity and a similar three-dimensional structure consisting of twelve β-strands folded into a β-barrel, with an internal thrice repeated structural motif.

There are three known IL-1 receptor subunits. The active receptor complex consists of the type I receptor and IL1RAcP (for IL-1 accessory protein). The type I receptor is responsible for binding of the three ligands, and is able to do so in the absence of the IL1RAcP. However, signal transduction requires interaction of IL-1α or β with the IL1RAcP. IL-1ra does not interact with the IL-1RAcP and hence cannot signal. A third receptor subunit, the type II receptor, binds IL-1α and IL-1β but cannot signal due to its lack of an intracellular domain. Rather, it acts as a decoy, either in its membrane form or as an antagonist in a cleaved secreted form, and hence inhibits IL-1 activity. It only weakly binds IL-1ra.

Many studies using IL-1ra, soluble IL-1R derived from the extracellular domain of the type I IL-1R, antibodies to IL-1α or β, and transgenic knockouts of these genes have shown conclusively that the IL-1s play a key role in a number of pathophysiologies (see C. A. Dinarello, Blood 87:2095–2147 (1996) for a review). For example, IL-1ra has been shown to be effective in animal models of septic shock, rheumatoid arthritis, graft versus host disease, stroke, cardiac ischemia, and is currently in clinical trials for some of these indications. Moreover, IL-1α and β have shown some potential as hematopoietic stem cell stimulators with potential as radio- and chemoprotectants.

More recently, a more distant member of the IL-1 family was identified. This protein, originally isolated through its ability to induce Interferon gamma in T cells and hence called Interferon gamma inducing factor (IGIF) [H. Okamura et al., Nature 378:88–91 (1995)], was subsequently shown to fold in a similar structure to the IL-1s and share weak amino acid identity [Bazan et al., Nature 379–591 (1996)]. The name IL-1γ was proposed, but the name IL-18 has been officially adopted. IGIF appears to play a direct role in the liver damage which occurs during toxic shock and is, therefore, like the other IL-1s in playing an early role in inflammatory and stressful conditions.

This indicates that the Interleukin-1 family has an established, proven history as therapeutical targets. Clearly there is a need for identification and characterization of further members of Interleukin-1 family which can play a role in preventing, ameliorating or correcting dysfunctions or diseases, including, but not limited to, chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease.

SUMMARY OF THE INVENTION

In one aspect, the invention relates to IL-1 delta polypeptides and recombinant materials and methods for their production. Another aspect of the invention relates to methods for using such IL-1 delta polypeptides and polynucleotides. Such uses include the treatment of chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease, among others. In still another aspect, the invention relates to methods to identify agonists and antagonists using the materials provided by the invention, and treating conditions associated with IL-1 delta imbalance with the identified compounds. Yet another aspect of the invention relates to diagnostic assays for detecting diseases associated with inappropriate IL-1 delta activity or levels.

DESCRIPTION OF THE INVENTION

Definitions

The following definitions are provided to facilitate understanding of certain terms used frequently herein.

"IL-1 delta" refers, among others, generally to a polypeptide having the amino acid sequence set forth in SEQ ID NO: 2 or an allelic variant thereof.

"IL-1 delta activity or IL-1 delta polypeptide activity" or "biological activity of the IL-1 delta or IL-1 delta polypeptide" refers to the metabolic or physiologic function of said IL-1 delta including similar activities or improved activities or these activities with decreased undesirable side-effects. Also included are antigenic and immunogenic activities of said IL-1 delta.

"IL-1 delta gene" refers to a polynucleotide having the nucleotide sequence set forth in SEQ ID NO: 1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated", but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquintination, and they may be cyclic, with or without branching. Cyclic, branched and branched cyclic polypeptides may result from posttranslation natural processes or may be made by synthetic methods. Modifications include acetylation, acrylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demthylation, formamation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, raceimization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182–626–646 and Rattan et al., "Protein Synthesis: Posttranslational Modifications Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds. Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1): 387), BLASTP, BLASTIN, FASTA (Atschul, S. F. et al., *J Molec Biol* (1990) (215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere in between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to IL-1 delta polypeptides (or IL-1 delta proteins). The IL-1 delta polypeptides include the polypeptide of SEQ ID NOS: 2 and 4; as well as polypeptides comprising the amino acid sequence of SEQ ID NO: 2; and polypeptides comprising the amino acid sequence which have at least 80% identity to that of SEQ ID NO: 2 over its entire identity to SEQ ID NO: 2. Furthermore, those with at least 97–99% are highly preferred. Also included within IL-1 delta polypeptides are polypeptides having the amino acid sequence which have at least 80% identity to the polypeptide having the amino acid sequence of SEQ ID NO: 2 over its entire length, and still more preferably at least 90% identity, and still more preferably at least 95% identity to SEQ ID NO: 2. Furthermore, those with at least 97–99% are highly preferred. Preferably IL-1 delta polypeptide exhibit at least one biological activity of IL-1 delta.

The IL-1 delta polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the IL-1 delta polypeptides are also included in the invention. A fragment is a polypeptide having an amino acid sequence that entirely is the same as part, but not all, of the amino acid sequence of the aforementioned IL-1 delta polypeptides. As with IL-1 delta polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of IL-1 delta polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of IL-1 delta polypeptides, except for deletion of a continuous series of residues that includes the amino terminus, or a continuous series of residues that includes the carboxyl terminus or deletion of two continuous series of resins, one including the amino terminus and one including the carboxyl terminus. Also preferred are fragments characterized by structural or functional attributes such as fragments that comprise alpha-helix and alpha-helix forming regions, belt-sheet and beta-sheet-forming regions, turn and turn-forming regions, coil and coil-forming regions, hydrogephilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate IL-1 delta activity, including those with a similar activity or an improved activity, or with a decreased undesirable activity. Also included are those that are antigenic or immunogenic in an animal, especially in a human.

Preferably, all of these polypeptide fragments retain the biological activity of the IL-1 delta, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The IL-1 delta polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to IL-1 delta polynucleotides. IL-1 delta polynucleotides include isolated polynucleotides which encode the IL-1 delta polypeptides and fragments, and polynucleotides closely related thereof. More specifically, IL-1 delta polynucleotide of the invention include a polynucleotide comprising the nucleotide sequence contained in SEQ ID NO: 1 encoding a IL-1 delta polypeptide of SEQ ID NO: 2, and polynucleotides having the particular sequences of SEQ ID NOS: 1 and 3. IL-1 delta polynucleotides further include a polynucleotide comprising a nucleotide sequence that has at least 80% identity over its entire length to a nucleotide sequence encoding the IL-1 delta polypeptide of SEQ ID NO: 2, and a polynucleotide comprising a nucleotide sequence that is at least 80% identical to that of SEQ ID NO: 1 over its entire length. In this regard, polynucleotides at least 90% identical are par- IL-1 delta of the invention is structurally related to other proteins of the Interleukin-1 family family, as shown by the results of sequencing the cDNA encoding IL-1 delta. The cDNA sequence of SEQ ID NO: 1 contains an open reading frame (nucleotide number 112 to 603) encoding a polypeptide of 164 amino acids of SEQ ID NO: 2. The amino acid sequence of Table 1 (SEQ ID NO: 2) has about 25.0% identity (using BESTFIT) in 156 amino acid residues with human IL-1beta (Auron et al., (1984) Proc. Natl. Acad. Sci USA 81:7907–7911; March et al., (1985) Nature 315:641–647). The nucleotide sequence of Table 1 (SEQ ID NO: 1) has about 67% identity (using BLAST) in 70 nucleotide residues with *Caenorhabditis elegans* cosmid F01D4. (Genbank accession number Z81054). Thus, IL-1 delta polypeptides and polynucleotides of the present invention are expected to have, inter alia, similar biological functions/properties to their homologous polypeptides and polynucleotides, and their utility is obvious to anyone skilled in the art.

TABLE 1[a]

| | |
|---|---|
| 1 | GGCACGAGGT TCCTCCCCAC TCTGTCTTTC TCACCTCTCC TTCACTTTTC |
| 51 | CTAGCCTCCT CACCACCATC TGATCTATCT TGTTCTCTTC ACAAAAGGCT |
| 101 | CTGAAGACAT CATGAACCCA CAACGGGAGG CAGCACCCAA ATCCTATGCT |
| 151 | ATTCGTGATT CTCGACAGAT GGTGTGGGTC CTGAGTGGAA ATTCTTTAAT |
| 201 | AGCAGCTCCT CTTAGCCGCA GCATTAAGCC TGTCACTCTT CATTTAATAG |
| 251 | CCTGTAGAGA CACAGAATTC AGTGACAAGG AAAAGGGTAA TATGGTTTAC |
| 301 | CTGGGAATCA AGGGAAAAGA TCTCTGTCTC TTCTGTGCAG AAATTCAGGG |
| 351 | CAAGCCTACT TTGCAGCTTA AGCTTCAGGG CTCCCAAGAT AACATAGGGA |
| 401 | AGGACACTTG CTGGAAACTA GTTGGAATTC ACACATGCAT AAACCTGGAT |
| 451 | GTGAGAGAGA GcTGCTTCAT GGGaACCCTT GACCAATGGG GAATAGGAGT |
| 501 | GGGTAGAAAG AAGTGGAAGA GTTCCTTTCA ACATCACCAT CTCAGGAAGA |
| 551 | AGGACAAAGA TTTCTCATCC ATGCGGACCA ACATAGGAAT GCCAGGAAGG |
| 601 | ATGTAGAAAT AAGGGGAGGA AGATTCCCAT CTCtACAATC TTtGAGTGGG |
| 651 | TTTGCTATCA ATGAAATGCT ACAAATGGAA TAAGTTGCAG AAATTTTTCT |
| 701 | CTTTTCTTGG GTTCTGGAGA GTTTGTAAAA CAAGGACACT ATGTATTTTT |
| 751 | AAAGAGTTGG TAAATCTTAC CTGTAAAGCT AGAGAAGGTC GGAGTCTTTT |
| 801 | TAGGAGTAGA TTTGGACTAC ATAACCTGTA AATGTGTTTT GTCCAGTCCT |
| 851 | TAGAGTGTTT TTTAAAAAAT TGTAAAGTCA AGGTTTTCAT GAAAAATGGG |
| 901 | GAAGATCAGA CAACATTGGT CCTGAATTCC CACAGAGCAG CAAGCTACTA |
| 951 | GAGCTCAATC TGTTATTTCT TTTCCTGATG AACAGGGGTT AAGTCCTATG |
| 1001 | GAAGAAACAG CAGAATTATT CAAAATTATT TACATAATGT GCAATTATTC |
| 1051 | ACTAGAGCAT GAGGAGTGAA ACGCTCTGTT TAGTATGTAT AACTTAAAAG |
| 1101 | GAACACATAC AATTAAAAGT AATTGAAAGA CATTTCTTCT TAAAAATTCT |
| 1151 | ATAATCTTAC ACTGGTAAAA TAAACTAGTT TTTCCCATGT |

[a]A nucleotide sequence of a human IL-1 delta (SEQ ID NO: 1).

TABLE 2[b]

| | |
|---|---|
| 1 | MNPQREAAPK SYAIRDSRQM VVVLSGNSLI AAPLSRSIKP VTLHLIACRD |
| 51 | TEFSDKEKGN MVYLGIKGKD LCLFCAEIQG KPTLQLKLQG SQDNIGKDTC |
| 101 | WKLVGIHTCI NLDVRESCFM GTLDQWGIGV GRKKWKSSFQ HHHLRKKDKD |
| 151 | FSSMRTNIGM PGRM |

[b]An amino acid sequence of a human IL-1 delta (SEQ ID NO: 2).

ticularly preferred, and those with at least 95% are especially preferred. Furthermore, those with at least 97% are highly preferred and those with at least 98–99% are most highly preferred, with at least 99% being the most preferred. Also included under IL-1 delta polynucleotides are a nucleotide sequence which has sufficient identity to a nucleotide sequence contained in SEQ ID NO: 1 to hybridize under conditions useable for amplification or for use as a probe or marker. The invention also provides polynucleotides which are complementary to such IL-1 delta polynucleotides.

One polynucleotide of the present invention encoding IL-1 delta may be obtained using standard cloning and screening, from a cDNA library derived from mRNA in cells of human osteoclastoma using the expressed sequence tag (EST) analysis (Adams, M. D., et al. *Science* (1991) 252:1651–1656; Adams, M. D. et al., *Nature* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding IL-1 delta polypeptide of SEQ ID NO: 2 may be identical to the polypeptide encoding sequence contained in Table 1 (nucleotide number 112 to 603 of SEQ ID NO: 1), or it may be a sequence, which as a result of the redundancy (degeneracy) of the genetic code, also encodes the polypeptide of SEQ ID NO: 2.

When the polynucleotides of the invention are used for the recombinant production of IL-1 delta polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding IL-1 delta variants comprising the amino acid sequence of IL-1 delta polypeptide of Table 2 (SEQ ID NO: 2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

than human) that have a high sequence similarity to the IL-1 delta gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50

In one embodiment, to obtain a polynucleotide encoding IL-1 delta polypeptide, including homologs and orthologs from species other than human, comprises the steps of screening an appropriate library under stingent hybridization conditions with a labeled probe having the SEQ ID NO: 1 or a fragment thereof (including that of SEQ ID NO: 3), and isolating full-length cDNA and genomic clones containing said polynucleotide sequence. Such hybridization techniques are well known to those of skill in the art. Thus in another aspect, IL-1 delta polynucleotides of the present invention further include a nucleotide sequence comprising a nucleotide sequence that hybridize under stringent condition to a nucleotide sequence having SEQ ID NO: 1 or a fragment thereof (including that of SEQ ID NO: 3). Also included with IL-1 delta polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA, followed by washing the filters in 0.1×SSC at about 65° C.

TABLE 3[c]

| | |
|---|---|
| 1 | GTTCCTCCCC ACTCTTTNTT TNTCACCTNT CCTTCACTTT TCCTAGCCTC |
| 51 | CTCACCACCA TCTGATCTAT CTNGTTCTCT TCACAAAAGG CTCTGAAGAC |
| 101 | ATCATGAACC CACAACGGGA GGCAGCACCC AANTCCTATG CTATTCGTGA |
| 151 | ATTCTNGACA GATGGTGTGG GTCCTGAGTG GAAATTNTTT AATAGCAGCT |
| 201 | CCTCTTAGCC GCAGCATTAA GCCTGTCACT CTTCATTTAA TAGCCTGTAG |
| 251 | AGACACAGAA TTCAGTGACA AGGAAAAGGG TAATATGGTT TACCTGGGGA |
| 301 | TCAAGGGAAA GATCTCTGGT |

[c]A partial nucleotide sequence of a human IL-1 delta (SEQ ID NO: 3).

TABLE 4[d]

| | |
|---|---|
| 1 | THNGRQHPXP MLFVNSXQMV WVLSGNXLIA APLSRSIKPV TLHLIACRDT |
| 51 | EFSDKEKGNM VYLGIKGKIS G |

[d]A partial amino acid sequence of a human IL-1 delta (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO: 1 or a fragment thereof (including that of SEQ ID NO: 3), may be used as hybridization probes for cDNA and genomic DNA, to isolate full-length cDNAs and genomic clones encoding IL-1 delta polypeptide and to isolate cDNA and genomic clones of other genes (including genes encoding homologs and orthologs from species other The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory mammals, such as Davis CLONING; A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid mediated transfection, electroporation, transduction, scrape loading, ballistic introduction or infection.

Representative examples of appropriate hosts include bacterial cells, such as streptococci, staphylococci, E. coli, Streptomyces and *Bacillus subtilis* cells; fungal cells, such as yeast cells and Aspergillus cells; insect cells such as Drosophila S2 Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the IL-1 delta polypeptide is to be expressed for use in screening assays, generally, it is preferred that the polypeptide be produced at the surface of the cell. In this event, the cells may be harvested prior to use in the screening assay. If IL-1 delta polypeptide is secreted into the medium, the medium can be recovered in order to recover and purify the polypeptide; if produced intracellularly, the cells must first be lysed before the polypeptide is recovered. IL-1 delta polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of IL-1 delta polynucleotides for use as diagnostic reagents. Detection of a mutated form of IL-1 delta gene associated with a dysfunction will provide a diagnostic tool that can add to or define a diagnosis of a disease or susceptibility to a disease which results from under-expression, over-expression or altered expression of IL-1 delta. Individuals carrying mutations in the IL-1 delta gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled IL-1 delta nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85:4397–4401. In another embodiment, an array of oligonucleotides probes comprising IL-1 delta nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610–613 (1996)).

The diagnostic assays offer a process for diagnosing or determining a susceptibility to chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease through detection of mutation in the IL-1 delta gene by the methods described.

In addition, chronic and acute inflammation, arthritis, septicemia, autoimmune disease (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease, can be diagnosed by methods comprising determining from a sample derived from a subject an abnormally decreased or increased level of IL-1 delta polypeptide or IL-1 delta mRNA. Decreased or increased expression can be measured at the RNA level using any of the methods well known in the art for the quantitation of polynucleotides, such as, for example, PCR, PT-PCR, RNase protection, Northern blotting and other hybridization methods. Assay techniques that can be used to determine levels of a protein, such as an IL-1 delta polypeptide, in a sample derived from a host are well-known to those of skill in the art. Such assay methods include radioimmunoassays, competitive-binding assays, Western Blot analysis and ELISA Assays.

Thus in another aspect, the present invention relates to a diagnostic kit for a disease or suspectability to a disease, particularly chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease, which comprises:

(a) a IL-1 delta polynucleotide, preferably the nucleotide sequence of SEQ ID NO: 1, or a fragment thereof;
(b) a nucleotide sequence complementary to that of (a);
(c) a IL-1 delta polypeptide, preferably the polypeptide of SEQ ID NO: 2, or a fragment thereof; or
(d) an antibody to a IL-1 delta polypeptide, preferably to the polypeptide of SEQ ID NO: 2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the IL-1 delta polypeptides. The term "immunospecific" means that the antibodies have substantiall greater affinity for the polypeptides of the invention than their affinity for other related polypeptides in the prior art.

Antibodies generated against the IL-1 delta polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 2:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against IL-1 delta polypeptides may also be employed to treat chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease, among others.

Vaccines

Another aspect of the invention relates to a method for inducing an immunological response in a mammal which comprises inoculating the mammal with IL-1 delta polypeptide, or a fragment thereof, adequate to produce antibody and/or T cell immune response to protect said animal from chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease, among others. Yet another aspect of the invention relates to a method of inducing immunological response in a mammal which comprises, delivering IL-1 delta polypeptide via a vector directing expression of IL-1 delta polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a IL-1 delta polypeptide wherein the composition comprises a IL-1 delta polypeptide or IL-1 delta gene. The vaccine formulation may further comprise a suitable carrier. Since IL-1 delta polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The IL-1 delta polypeptide of the present invention may be employed in a screening process for compounds which activate (agonists) or inhibit activation of (antagonists, or otherwise called inhibitors) the IL-1 delta polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., Current Protocols in Immunology 1(2): Chapter 5 (1991).

IL-1 delta polypeptides are responsible for many biological functions, including many pathologies. Accordingly, it is desirous to find compounds and drugs which stimulate IL-1 delta polypeptide on the one hand and which can inhibit the function of IL-1 delta polypeptide on the other hand. In general, agonists are employed for therapeutic and prophylactic purposes for such conditions as chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease. Antagonists may be employed for a variety of therapeutic and prophylactic purposes for such conditions as chronic and acute inflammation, arthritis, septicemia, autoimmune diseases (e.g. inflammatory bowel disease, psoriasis), transplant rejection, graft versus host disease, infection, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease.

In general, such screening procedures may involve using appropriate cells which express the IL-1 delta polypeptide or respond to IL-1 delta polypeptide of the present invention. Such cells include cells from mammals, yeast, Drosophila or E. coli. Cells which express the IL-1 delta polypeptide (or cell membrane containing the expressed polypeptide) or respond to IL-1 delta polypeptide are then contacted with a test compound to observe binding, or stimulation or inhibition of a functional response. The ability of the cells which were contacted with the candidate compounds is compared with the same cells which were not contacted for IL-1 delta activity.

The IL-1 delta cDNA, protein and antibodies to the protein may also be used to configure assays for detecting the effect of added compounds on the production of IL-1 delta mRNA and protein in cells. For example, an ELISA may be constructed for measuring secreted or cell associated levels of IL-1 delta protein using monoclonal and polyclonal antibodies by standard methods known in the art, and this can be used to discover agents (i.e. antagonists or agonists) which may inhibit or enhance the production of IL-1 delta from suitably manipulated cells or tissues.

The IL-1 delta protein may be used to identify membrane bound or soluble receptors through standard receptor binding techniques known in the art. These include, but are not limited to, ligand binding and crosslinking assays in which the IL-1 delta is labeled with a radioactive isotope (eg $^{125}$I), chemically modified (e.g. biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopyl. In adding to being used for purification and cloning of the receptor, these binding assays can be used to identify agonists and antagonists of IL-1 delta which compete with the binding of IL-1 delta to its receptors. The above binding assays can be used to identify cells which respond biologically to IL-1 delta. Cells which respond to IL-1 delta may show changes in intracellular signal transduction pathways and in gene expression. These changes can be used in screens for agonists or antagonists which mimic or inhibit the action of IL-1 delta, respectively.

The assays may simply test binding of a candidate compound wherein adherence to the cells bearing the IL-1 delta polypeptide is detected by means of a label directly or indirectly associated with the candidate compound or in an assay involving competition with a labeled competitor. Further, these assays may test whether the candidate compound results in a signal generated by activation of the IL-1 delta polypeptide, using detection systems appropriate to the cells bearing the IL-1 delta polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a IL-1 delta polypeptide to form a mixture, measuring IL-1 delta activity in the mixture, and comparing the IL-1 delta activity of the mixture to a standard.

The IL-1 delta cDNA, protein and antibodies to the protein may also be used to configure assays for detecting the effect of added compounds on the production of IL-1 delta mRNA and protein in cells. For example, an ELISA may be constructed for measuring secreted or cell associated levels of IL-1 delta protein using monoclonal and polyclonal antibodies by standard methods known in the art, and this can be used to discover agents which may inhibit or enhance the production of IL-1 delta (also called antagonist or agonist, respectively) from suitably manipulated cells or tissues.

The IL-1 delta protein may be used to identify membrane bound or soluble receptors, if any, through standard receptor binding techniques known in the art. These include, but are not limited to, ligand binding and crosslinking assays in which the IL-1 delta is labeled with a radioactive isotope (eg. 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of IL-1 delta which compete with the binding of IL-1 delta to its receptors, if any. Standard method for conducting screening assays are well understood in the art.

Examples of potential IL-1 delta polypeptide antagonists include antibodies or, in some cases, oligonucleotides or proteins which are closely related to the ligands, substrates, enzymes, receptors, etc., as the case may be, of the IL-1 delta polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for IL-1 delta polypeptides; or compounds which decrease or enhance the production of IL-1 delta polypeptides, which comprises:

(a) a IL-1 delta polypeptide, preferably that of SEQ ID NO: 2;

(b) a recombinant cell expressing a IL-1 delta polypeptide, preferably that of SEQ ID NO: 2;

(c) a cell membrane expressing a IL-1 delta polypeptide; preferably that of SEQ ID NO: 2; or (d) antibody to a IL-1 delta polypeptide, preferably that of SEQ ID NO: 2.

It will be appreciated that in any such kit, (a), (b), (c) or (d) may comprise a substantial component.

Prophylactic and Therapeutic Methods

This invention provides methods of treating abnormal conditions such as, chronic and acute inflammation, arthritis, septicemia, autoimmune diseases (e.g. inflammatory bowel disease, psoriasis), transplant rejection, graft versus host disease, stroke, ischemia, acute respiratory disease syndrome, restenosis, brain injury, AIDS, bone diseases (e.g. osteoporosis), cancer (e.g. lymphoproliferative disorders), atherosclerosis, and Alzheimer's disease, related to both an excess of and insufficient amounts of IL-1 delta polypeptide activity.

If the activity of IL-1 delta polypeptide is in excess, several approaches are available. One approach comprises administering to a subject an inhibitor compound (antagonist) as hereinabove described along with a pharmaceutically acceptable carrier in an amount effective to inhibit the function of the IL-1 delta polypeptide, such as, for example, by blocking the binding of ligands, substrates, enzymes, receptors, etc., or by inhibiting a second signal, and thereby alleviating the abnormal condition. In another approach, soluble forms of IL-1 delta polypeptides still capable of binding the ligand, substrate, enzymes, receptors, etc. in competition with endogenous IL-1 delta polypeptide may be administered. Typical embodiments of such competitors comprise fragments of the IL-1 delta polypeptide.

In another approach, soluble forms of IL-1 delta polypeptides still capable of binding the ligand in competition with endogenous IL-1 delta polypeptide may be administered. Typical embodiments of such competitors comprise fragments of the IL-1 delta polypeptide.

In still another approach, expression of the gene encoding endogenous IL-1 delta polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of IL-1 delta and its activity, several approaches are also available. One approach comprises administering to a subject a therapeutically effective amount of a compound which activates IL-1 delta polypeptide, i.e., an agonist as described above, in combination with a pharmaceutically acceptable carrier, to thereby alleviate the abnormal condition. Alternatively, gene therapy may be employed to effect the endogenous production of IL-1 delta by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of IL-1 delta polypeptides in combination with a suitable pharmaceutical carrier.

Formulation and Administration

Peptides, such as the soluble form of IL-1 delta polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route or administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

EXAMPLE 1

A partial clone encoding IL-1 delta was identified through a search of a commercial database using the amino acid sequence of a previously identified novel member of the IL-1 family, IL-1ra $\beta$, which is unpublished but has been submitted in a previous patent application (U.S. Ser. No. 08/790,032). The partial sequence of this clone shared 34.8% amino acid identity with IL-1ra $\beta$, and 25.8% identity with human IL-1$\beta$ (Auron et al., Proc. Natl. Aca. Sci. USA 81:7907–7911 (1984); C. J. March et al, Nature 315:641–647 (1985)). The clone encoding IL-1δ was found in an osteoclastoma cell library.

EXAMPLE 2

Although there are several methods to obtain the full length cDNA, two are outlined below.

1.) The method of Rapid Amplification of cDNA Ends (RACE) can be utilized to obtain the 5' end. See Frohman et al., Proc. Nat. Acad. Sci USA 85, 8998–9002 (1988). Briefly, specific oligonucleotides are annealed to mRNA and used to prime the synthesis of the cDNA strand. Following destruction of the mRNA with RNaseH, a poly-C anchor sequence is added to the 3' end of the cDNA and the resulting fragment is amplified using a nested set of antisense primers and an anchor sequence primer. The amplified fragment is cloned into an appropriate vector and subjected to restriction and sequence analysis.

2.) The polymerase chain reaction can be used to amplify the 5' end of the cDNA from human cDNA libraries using sequential rounds of nested PCR with two sets of primers. One set of antisense primers is specific to the 5' end of the partial cDNA and the other set of primers anneals to vector specific sequence. The amplified products are cloned into an appropriate vector and subjected to restriction and sequence analysis.

All publications, including but not limited to patent and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence has at least 95% identity over its entire length to a nucleotide sequence encoding the polypeptide of SEQ ID NO: 2, said identity being calculated using FASTA wherein the two sequences are maximally aligned so that highest order match between the sequences is obtained.

2. The isolated polynucleotide of claim 1 comprising a nucleotide sequence encoding the polypeptide of SEQ ID NO: 2.

3. An isolated polynucleotide comprising a nucleotide sequence which has at least 95% identity to SEQ ID NO: 1, said identity being over the entire length of SEQ ID NO: 1 and calculated using FASTA wherein sequences are maximally aligned so that highest order match between the sequences is obtained.

4. The isolated polynucleotide of claim 3 having the nucleotide sequence of SEQ ID NO: 1.

5. The isolated polynucleotide of claim 4 wherein said nucleotide sequence comprises nucleotides 112 to 603 of SEQ ID NO: 1.

6. An isolated polynucleotide which is complementary to the polynucleotide of any one of claims 1, 2, 3, 4, or 5.

7. An expression system comprising a polynucleotide of claim 2 capable of producing a polypeptide comprising an amino acid sequence of SEQ ID NO: 2 when said expression system is present in a compatible host cell.

8. A process for producing a recombinant host cell comprising transforming or transfecting a cell with the expression system of claim 7 such that the host cell, under appropriate culture conditions, produces a polypeptide comprising an amino acid sequence of SEQ ID NO: 2.

9. A recombinant host cell produced by the process of claim 7.

10. A membrane of a recombinant host cell of claim 9 expressing a polypeptide comprising an amino acid sequence of SEQ ID NO: 2.

11. A process for producing a polypeptide comprising culturing the recombinant host cell of claim 9 under conditions sufficient for the production of said polypeptide and recovering the polypeptide from the culture.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1190 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GGCACGAGGT TCCTCCCCAC TCTGTCTTTC TCACCTCTCC TTCACTTTTC CTAGCCTCCT        60

CACCACCATC TGATCTATCT TGTTCTCTTC ACAAAAGGCT CTGAAGACAT CATGAACCCA       120

CAACGGGAGG CAGCACCCAA ATCCTATGCT ATTCGTGATT CTCGACAGAT GGTGTGGGTC       180

CTGAGTGGAA ATTCTTTAAT AGCAGCTCCT CTTAGCCGCA GCATTAAGCC TGTCACTCTT       240

CATTTAATAG CCTGTAGAGA CACAGAATTC AGTGACAAGG AAAAGGGTAA TATGGTTTAC       300

CTGGGAATCA AGGGAAAAGA TCTCTGTCTC TTCTGTGCAG AAATTCAGGG CAAGCCTACT       360

TTGCAGCTTA AGCTTCAGGG CTCCCAAGAT AACATAGGGA AGGACACTTG CTGGAAACTA       420

GTTGGAATTC ACACATGCAT AAACCTGGAT GTGAGAGAGA GCTGCTTCAT GGGAACCCTT       480

GACCAATGGG GAATAGGAGT GGGTAGAAAG AAGTGGAAGA GTTCCTTTCA ACATCACCAT       540

CTCAGGAAGA AGGACAAAGA TTTCTCATCC ATGCGGACCA ACATAGGAAT GCCAGGAAGG       600

ATGTAGAAAT AAGGGGAGGA AGATTCCCAT CTCTACAATC TTTGAGTGGG TTTGCTATCA       660

ATGAAATGCT ACAAATGGAA TAAGTTGCAG AAATTTTTCT CTTTTCTTGG GTTCTGGAGA       720

GTTTGTAAAA CAAGGACACT ATGTATTTTT AAAGAGTTGG TAAATCTTAC CTGTAAAGCT       780

AGAGAAGGTC GGAGTCTTTT TAGGAGTAGA TTTGGACTAC ATAACCTGTA AATGTGTTTT       840

GTCCAGTCCT TAGAGTGTTT TTTAAAAAAT TGTAAAGTCA AGGTTTTCAT GAAAAATGGG       900

GAAGATCAGA CAACATTGGT CCTGAATTCC CACAGAGCAG CAAGCTACTA GAGCTCAATC       960

TGTTATTTCT TTTCCTGATG AACAGGGGTT AAGTCCTATG GAAGAAACAG CAGAATTATT      1020

CAAAATTATT TACATAATGT GCAATTATTC ACTAGAGCAT GAGGAGTGAA ACGCTCTGTT      1080

TAGTATGTAT AACTTAAAAG GAACACATAC AATTAAAAGT AATTGAAAGA CATTTCTTCT      1140
```

TAAAAATTCT ATAATCTTAC ACTGGTAAAA TAAACTAGTT TTTCCCATGT                1190

(2) INFORMATION FOR SEQ ID NO:2:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Asn Pro Gln Arg Glu Ala Ala Pro Lys Ser Tyr Ala Ile Arg Asp
 1               5                  10                  15

Ser Arg Gln Met Val Trp Val Leu Ser Gly Asn Ser Leu Ile Ala Ala
             20                  25                  30

Pro Leu Ser Arg Ser Ile Lys Pro Val Thr Leu His Leu Ile Ala Cys
         35                  40                  45

Arg Asp Thr Glu Phe Ser Asp Lys Glu Lys Gly Asn Met Val Tyr Leu
     50                  55                  60

Gly Ile Lys Gly Lys Asp Leu Cys Leu Phe Cys Ala Glu Ile Gln Gly
 65                  70                  75                  80

Lys Pro Thr Leu Gln Leu Lys Leu Gln Gly Ser Gln Asp Asn Ile Gly
                 85                  90                  95

Lys Asp Thr Cys Trp Lys Leu Val Gly Ile His Thr Cys Ile Asn Leu
            100                 105                 110

Asp Val Arg Glu Ser Cys Phe Met Gly Thr Leu Asp Gln Trp Gly Ile
        115                 120                 125

Gly Val Gly Arg Lys Lys Trp Lys Ser Ser Phe Gln His His His Leu
    130                 135                 140

Arg Lys Lys Asp Lys Asp Phe Ser Ser Met Arg Thr Asn Ile Gly Met
145                 150                 155                 160

Pro Gly Arg Met
```

(2) INFORMATION FOR SEQ ID NO:3:

(i) SEQUENCE CHARACTERISTICS:
        (A) LENGTH: 320 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GTTCCTCCCC ACTCTTTNTT TNTCACCTNT CCTTCACTTT TCCTAGCCTC CTCACCACCA          60

TCTGATCTAT CTNGTTCTCT TCACAAAAGG CTCTGAAGAC ATCATGAACC CACAACGGGA         120

GGCAGCACCC AANTCCTATG CTATTCGTGA ATTCTNGACA GATGGTGTGG GTCCTGAGTG         180

GAAATTNTTT AATAGCAGCT CCTCTTAGCC GCAGCATTAA GCCTGTCACT CTTCATTTAA         240

TAGCCTGTAG AGACACAGAA TTCAGTGACA AGGAAAAGGG TAATATGGTT TACCTGGGGA         300

TCAAGGGAAA GATCTCTGGT                                                     320

(2) INFORMATION FOR SEQ ID NO:4:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Thr His Asn Gly Arg Gln His Pro Xaa Pro Met Leu Phe Val Asn Ser
1               5                   10                  15

Xaa Gln Met Val Trp Val Leu Ser Gly Asn Xaa Leu Ile Ala Ala Pro
            20                  25                  30

Leu Ser Arg Ser Ile Lys Pro Val Thr Leu His Leu Ile Ala Cys Arg
        35                  40                  45

Asp Thr Glu Phe Ser Asp Lys Glu Lys Gly Asn Met Val Tyr Leu Gly
    50                  55                  60

Ile Lys Gly Lys Ile Ser Gly
65                  70
```